United States Patent
Zhang (10) Patent No.: US 11,455,546 B2
(45) Date of Patent: Sep. 27, 2022

(54) METHOD AND APPARATUS FOR AUTOMATICALLY DISCOVERING MEDICAL KNOWLEDGE

(71) Applicant: BOE TECHNOLOGY GROUP CO., LTD., Beijing (CN)

(72) Inventor: Zhenzhong Zhang, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 1157 days.

(21) Appl. No.: 15/779,709

(22) PCT Filed: Sep. 12, 2017

(86) PCT No.: PCT/CN2017/101387
§ 371 (c)(1),
(2) Date: May 29, 2018

(87) PCT Pub. No.: WO2018/161516
PCT Pub. Date: Sep. 13, 2018

(65) Prior Publication Data
US 2020/0034719 A1    Jan. 30, 2020

(30) Foreign Application Priority Data
Mar. 7, 2017   (CN) .......................... 201710131491.7

(51) Int. Cl.
*G06F 17/00* (2019.01)
*G06N 5/02* (2006.01)
(Continued)

(52) U.S. Cl.
CPC ............. *G06N 5/022* (2013.01); *G06F 40/10* (2020.01); *G06F 40/30* (2020.01); *G16H 10/60* (2018.01); *G16H 50/20* (2018.01); *G16H 50/70* (2018.01)

(58) Field of Classification Search
CPC ......... G06F 40/10; G06F 40/30; G16H 10/60; G16H 50/20; G16H 50/70; G16H 70/20
See application file for complete search history.

(56) References Cited

U.S. PATENT DOCUMENTS 8,140,550 B2    3/2012   Varadarajan et al.
10,346,751 B2 *  7/2019   Agarwal .............. G06F 16/9024
(Continued)

FOREIGN PATENT DOCUMENTS

CN       101681348 A     3/2010
CN       101944099 A     1/2011
(Continued)

OTHER PUBLICATIONS

Xun, Guangxu, et al. "Generating medical hypotheses based on evolutionary medical concepts." 2017 IEEE International Conference on Data Mining (ICDM). IEEE, 2017 (Year: 2017).*
(Continued)

*Primary Examiner* — Andrew T McIntosh
(74) *Attorney, Agent, or Firm* — Dave Law Group LLC; Raj S. Dave (57) ABSTRACT

Embodiments of the present disclosure provide a method and an apparatus for automatically discovering medical knowledge. In this method, one or more linking concepts having a semantic relation with a starting concept are obtained from a medical literature library. The starting concept represents a disease. Next, one or more target concepts having a semantic relation with the one or more linking concepts are obtained from the medical literature library, and an association degree of each of the one or more target concepts with respect to the starting concept is calculated. The association degree indicates a probability that the target concept can cope with the starting concept. Further, the one or more target concepts are sorted according to the calculated association degrees. In this method,
(Continued)

explainable target concepts can be obtained by using semantic analysis, and these target concepts are sorted to increase a possibility of discovering useful medical knowledge.

18 Claims, 6 Drawing Sheets

(51) Int. Cl.
*G16H 10/60* (2018.01)
*G16H 50/70* (2018.01)
*G16H 50/20* (2018.01)
*G06F 40/10* (2020.01)
*G06F 40/30* (2020.01)

(56) References Cited

U.S. PATENT DOCUMENTS

| | | | |
|---|---|---|---|
| 2008/0109212 | A1 | 5/2008 | Witbrock et al. |
| 2009/0192954 | A1* | 7/2009 | Katukuri ............... G16H 50/70 706/46 |
| 2011/0251984 | A1* | 10/2011 | Nie ........................ G06Q 10/10 706/18 |
| 2015/0019462 | A1 | 1/2015 | De et al. |
| 2015/0046388 | A1* | 2/2015 | Sheth ..................... G06N 5/022 706/55 |
| 2016/0012336 | A1* | 1/2016 | Franceschini ....... G06F 16/3334 706/55 |

FOREIGN PATENT DOCUMENTS

| | | |
|---|---|---|
| CN | 102214189 A | 10/2011 |
| CN | 103678418 A | 3/2014 |
| CN | 103761264 A | 4/2014 |
| CN | 104239513 A | 12/2014 |
| EP | 0478315 A2 | 4/1992 |
| WO | 2010/055968 A1 | 5/2010 |
| WO | 2015042930 A1 | 4/2015 |

OTHER PUBLICATIONS

Xun, Guangxu, et al. "Generating medical hypotheses based on evolutionary medical concepts." 2017 IEEE International Conference on Data Mining (ICDM). IEEE, 2017 (Year: 2010).*
De Vine, Lance, et al. "Medical semantic similarity with a neural language model." Proceedings of the 23rd ACM international conference on conference on information and knowledge management. 2014 (Year: 2014).*
European Search Report dated Dec. 9, 2020 for EP Application No. 17870626.
He, S., et al., "CASIA@V2: A MLN-based Question Answering System over Linked Data," CLEF 2014 Labs and Workshops, Notebook Papers. CEUR Workshop Proceedings, 2014, pp. 1249-1259.
Richardson, K. and Kuhn, J., "Learning to Make Influences in a Semantic Parsing Task," Transactions of the Association for Computational Linguistics, vol. 4, May 2016, pp. 155-168.
Office action issued in Chinese Application No. 201710131491.7, dated May 7, 2020, 23 pages.
"Knowledge Discovery in Biomedical Literature using Semantic Resources and Supervised Machine Learning" dated Dec. 20, 2010, 89 pages.
Liu Xiang, "Research on Domain knowledge Learning and Update Technology based on Markov Logic Network", dated Jun. 2014, 83 pages.
Hong-Yu Kang et al."Knowledge discovery and data integration in biomedical literature", dated Feb. 2015, 15 pages, 1672-3982.
Xing Wang et al. "Network Public Opinion Guiding based on Markov Logic Networks", dated Jun. 2015, vol. 5—No. 3, Intelligent Computer and Applications.
Xiaohua Hu, "Mining Hidden Connections Among Biomedical Concepts from Disjoint Biomedical Literature Sets Through Semantic-Based Association Rule", 2009, vol. 25, 207-223.
International Search Report from PCT Application No. PCT/CN2017/101387 dated Dec. 20, 2017 (4 pages).
Written Opinion from PCT Application No. PCT/CN2017/101387 dated Dec. 20, 2017 (3 pages).
Cameron, Delroy et al., A Graph-Based Recovery And Decomposition of Swanson's Hypothesis Using Semantic Predications, Journal of Biomedical Informatics, 2013, p. 238-251, vol. 46.
Hristovski, Dimitar et al., Exploiting Semantic Relations for Literature-Based Discovery, Feb. 2006; 6 pages.
Gordon, Michael D et al., Toward Discovery Support Systems: A Replication, Re-Examination, and Extension of Swanson's Work on Literature-Based Discovery of a Connection between Raynaud's and Fish Oil; Feb. 1996; p. 116-128.
Swanson, Don R, Fish Oil, Raynaud's Syndrome, and Undiscovered Public Knowledge, Perspectives in Biology and Medicine, 1986, vol. 30, No. 1; 13 pages.
Yetisgen-Yildiz, Meliha et al., Using Statistical and Knowledge-Based Approaches for Literature-Based Discovery, Journal of Biomedical Information, vol. 39,2006, p. 600-611.

* cited by examiner

METHOD AND APPARATUS FOR AUTOMATICALLY DISCOVERING MEDICAL KNOWLEDGE

CROSS-REFERENCE TO RELATED APPLICATION

This application claims the benefit and priority of Chinese Patent Application No. 201710131491.7 filed on Mar. 7, 2017, the entire content of which is incorporated herein by reference as a part of the present application.

TECHNICAL FIELD

The present disclosure relates to the field of artificial intelligence, and more particularly, to a method and an apparatus for automatically discovering medical knowledge.

BACKGROUND

Nowadays, the quantity of medical literatures is growing exponentially. For example, MEDLINE, a medical literature database, stores more than 20 million medical literatures, and millions of medical literatures are increasing every year. Since the quantity of medical literatures is large, it is difficult to discover associated information among different literatures, thus missing an opportunity to discover important medical knowledge.

To automatically discover potentially useful information from a large quantity of medical literatures, in 1986, Professor Swanson from the University of Chicago proposed a disjoint Literature-based Discovery (LBD) method, i.e., an ABC model. In the ABC model, C is used as a starting concept and used for representing a disease, B is used as a linking concept, and A is used as a target concept and used for representing a substance (or drug) that may cure the disease C. The main idea of the ABC model is to extract knowledge fragments from two disjoint literatures and combine the knowledge fragments together to discover new potential knowledge. Specifically, for the two disjoint literatures: the Literature 1 on Raynaud's disease and the Literature 2 on fish oil, it is discovered by text analysis that the majority of patients suffering from the Raynaud's disease (i.e., the starting concept C) as mentioned in the Literature 1 have specific physiological phenomena (i.e., the link concept B), such as, increased blood viscosity, increased platelet aggregation, and vasoconstriction, etc. In addition, it is discovered in the Literature 2 that the fish oil (i.e., the target concept A) and active ingredients thereof can reduce the blood viscosity and the platelet aggregation and enable vasodilation. Based on the above discovery, Professor Swanson drew a conclusion (or hypothesis) that the fish oil can cure the Raynaud's disease, and validated the conclusion in subsequent medical clinical trials.

Some LBD methods may be based on statistical information of co-occurrence of concepts, and it is assumed that: the higher the number of co-occurrences of the concept A and the concept B is, the more likely the concept A is associated with the concept B. This method implements the ABC model by using statistical features. For example, potential values of noun phrases may be determined by using four statistics based on frequency statistical information of the phrases, and the potential values are sorted and selected. For another example, the association degrees between the linking concepts and the target concepts are evaluated by using statistical information of Z-Score, TF-IDF, PMI and so on, and the concepts are filtered. However, the method of knowledge discovery based on statistical information has the following problems: 1) a lot of useless target concepts are generated, thus it is difficult to discover useful knowledge; and 2) no semantic resource is used, and thus it is impossible to give a reasonable explanation to the obtained knowledge discovery.

Further, to explain the discovered knowledge, a semantic relation is introduced in the LBD method. For example, medical literatures may be analyzed by using a natural language processing technology to obtain the semantic relation in each sentence and define an association rule, such that explainable discoveries may be obtained. For another example, the ABC model is extended by introducing semantic relations into graph models. These methods of introducing semantic relations can explain the discovered target concepts, but cannot distinguish the importance of knowledge.

SUMMARY

In view of the above technical problems, embodiments of the present disclosure provide a method and an apparatus for automatically discovering medical knowledge, which can automatically discover useful medical knowledge from medical literatures.

A first aspect of the present disclosure provides a method for automatically discovering medical knowledge. In this method, one or more linking concepts having a semantic relation with a starting concept are obtained from a medical literature library. The starting concept represents a disease. Next, one or more target concepts having a semantic relation with the one or more linking concepts are obtained from the medical literature library, and an association degree of each of the one or more target concepts with respect to the starting concept is calculated. The association degree indicates a probability that the target concept can cope with the starting concept. The one or more target concepts are sorted according to the calculated association degrees.

In embodiments of the present disclosure, in the step of calculating the association degree of each of the one or more target concepts with respect to the starting concept, for each of the one or more target concepts, a linking concept related to the target concept in the one or more linking concepts is determined as a related linking concept. Next, the association degree of the target concept with respect to the starting concept is calculated based on a first semantic relation between the related linking concept and the starting concept and a second semantic relation between the related linking concept and the target concept by using a pretrained Markov logic network. The Markov logic network is composed of predefined predicates and logic formulas describing a logic relation among the predicates.

In embodiments of the present disclosure, the association degree of the target concept with respect to the starting concept is calculated as below:

$$P = \frac{1}{Z}\exp(\Sigma_i\ w_i f_i)$$

wherein P represents the association degree, Z represents a normalization factor, $f_i$ represents the $i^{th}$ logic formula, and $w_i$ represents a weight for the $i^{th}$ logic formula.

In embodiments of the present disclosure, the method further provides a logic relation between each of the one or more target concepts and the starting concept.

In embodiments of the present disclosure, in the step of providing a logic relation between each of the one or more target concepts and the starting concept, for each of the one or more target concepts, a logic formula including the first semantic relation and the second semantic relation is determined as the logic relation. Next, the logic relation is recorded in association with the target concept.

In embodiments of the present disclosure, in the step of obtaining one or more linking concepts having the semantic relation with the starting concept from the medical literature library, a sentence containing the starting concept is retrieved from the medical literature library, and the semantic relation contained in the sentence is extracted. Next, the one or more linking concepts are determined based on the semantic relation.

In embodiments of the present disclosure, the obtained linking concepts are further filtered to obtain the linking concepts having a predetermined semantic relation.

In embodiments of the present disclosure, in the step of obtaining one or more target concepts having the semantic relation with the one or more linking concepts from the medical literature library, for each of the one or more linking concepts, a sentence containing the linking concept is retrieved from the medical literature library, and the semantic relation contained in the sentence is extracted. Next, the target concept is determined based on the semantic relation.

In embodiments of the present disclosure, the one or more target concepts are sorted according to a descending order of the corresponding association degrees.

A second aspect of the present disclosure provides a system for automatically discovering medical knowledge. The system includes a first obtaining apparatus, a second obtaining apparatus, a calculating apparatus, and a sorting apparatus. The first obtaining apparatus is configured to obtain one or more linking concepts having a semantic relation with a starting concept from a medical literature library. The starting concept represents a disease. The second obtaining apparatus is configured to obtain one or more target concepts having a semantic relation with the one or more linking concepts from the medical literature library. The calculating apparatus is configured to calculate an association degree of each of the one or more target concepts with respect to the starting concept. The association degree indicates a probability that the target concept can cope with the starting concept. The sorting apparatus is configured to sort the one or more target concepts according to the calculated association degrees.

In embodiments of the present disclosure, the calculating apparatus includes: a determining module, configured to determine, for each of the one or more target concepts, a linking concept related to the target concept in the one or more linking concepts as a related linking concept; and a calculating module, configured to calculate the association degree of the target concept with respect to the starting concept based on a first semantic relation between the related linking concept and the starting concept and a second semantic relation between the related linking concept and the target concept by using a pretrained Markov logic network. The Markov logic network is composed of predefined predicates and logic formulas describing a logic relation among the predicates.

In embodiments of the present disclosure, the system further includes: a providing apparatus, configured to provide a logic relation between each of the one or more target concepts and the starting concept.

In embodiments of the present disclosure, the providing apparatus includes: a logic relation determining module, configured to determine, for each of the one or more target concepts, a logic formula including the first semantic relation and the second semantic relation as the logic relation; and a recording module, configured to record the logic relation in association with the target concept.

In embodiments of the present disclosure, the first obtaining apparatus includes: a retrieving module, configured to retrieve a sentence containing the starting concept from the medical literature library; an extracting module, configured to extract the semantic relation contained in the sentence; and a determining module, configured to determine the one or more linking concepts based on the semantic relation.

In embodiments of the present disclosure, the first obtaining apparatus further includes: a filtering module, configured to filter the obtained linking concepts to obtain the linking concepts having a predetermined semantic relation.

In embodiments of the present disclosure, the second obtaining apparatus includes: a retrieving module, configured to retrieve, for each of the one or more linking concepts, a sentence containing the linking concept from the medical literature library; an extracting module, configured to extract the semantic relation contained in the sentence; and a determining module, configured to determine the target concept based on the semantic relation.

In embodiments of the present disclosure, the sorting apparatus is configured to sort the one or more target concepts according to a descending order of the corresponding association degrees.

A third aspect of the present disclosure provides an apparatus for automatically discovering medical knowledge. The apparatus includes at least one processor and at least one memory storing a computer program. When the computer program is executed by the at least one processor, the apparatus is caused to: obtain one or more linking concepts having a semantic relation with a starting concept from a medical literature library, wherein the starting concept represents a disease; obtain one or more target concepts having a semantic relation with the one or more linking concepts from the medical literature library; calculate an association degree of each of the one or more target concepts with respect to the starting concept, wherein the association degree indicates a probability that the target concept can cope with the starting concept; and sort the one or more target concepts according to the calculated association degrees.

In embodiments of the present disclosure, when the computer program is executed by the at least one processor, the apparatus is caused to calculate the association degree of each of the one or more target concepts with respect to the starting concept by the following operations: for each of the one or more target concepts, determining a linking concept related to the target concept in the one or more linking concepts as a related linking concept; and calculating the association degree of the target concept with respect to the starting concept based on a first semantic relation between the related linking concept and the starting concept and a second semantic relation between the related linking concept and the target concept by using a pretrained Markov logic network. The Markov logic network is composed of predefined predicates and logic formulas describing a logic relation among the predicates.

In embodiments of the present disclosure, the association degree of the target concept with respect to the starting concept is calculated as below:

$$P = \frac{1}{Z}\exp(\Sigma_i\ w_i f_i)$$

wherein P represents the association degree, Z represents a normalization factor, $f_i$ represents the $i^{th}$ logic formula, and $w_i$ represents a weight for the $i^{th}$ logic formula.

In embodiments of the present disclosure, when the computer program is executed by the at least one processor, the apparatus is further caused to provide a logic relation between each of the one or more target concepts and the starting concept.

In embodiments of the present disclosure, when the computer program is executed by the at least one processor, the apparatus is caused to provide a logic relation between each of the one or more target concepts and the starting concept by the following operations: for each of the one or more target concepts, determining a logic formula including the first semantic relation and the second semantic relation as the logic relation; and recording the logic relation in association with the target concept.

In embodiments of the present disclosure, when the computer program is executed by the at least one processor, the apparatus is caused to obtain one or more linking concepts having the semantic relation with the starting concept from the medical literature library by the following operations: retrieving a sentence containing the starting concept from the medical literature library; extracting the semantic relation contained in the sentence; and determining the one or more linking concepts based on the semantic relation.

In embodiments of the present disclosure, when the computer program is executed by the at least one processor, the apparatus is further caused to obtain one or more linking concepts having the semantic relation with the starting concept from the medical literature library by the following operation: filtering the obtained linking concepts to obtain the linking concepts having a predetermined semantic relation.

In embodiments of the present disclosure, when the computer program is executed by the at least one processor, the apparatus is caused to obtain one or more target concepts having the semantic relation with the one or more linking concepts from the medical literature library by the following operations: for each of the one or more linking concepts, retrieving a sentence containing the linking concept from the medical literature library; extracting the semantic relation contained in the sentence; and determining the target concept based on the semantic relation.

In embodiments of the present disclosure, when the computer program is executed by the at least one processor, the apparatus is caused to sort the one or more target concepts according to a descending order of the corresponding association degrees.

A fourth aspect of the present disclosure provides a computer readable storage medium storing a computer program. When the computer program is executed by a processor, the steps of the aforementioned method for automatically discovering medical knowledge are carried out.

By using the method according to the embodiments of the present disclosure, the discovered medical knowledge can be sorted, such that the probability of discovering useful medical knowledge can be improved, which is benefit to further analysis. Furthermore, by using the method according to the embodiments of the present disclosure, a logical explanation of the relation between the starting concept and the target concept can be provided, such that the explainability of the discovered medical knowledge is enhanced.

BRIEF DESCRIPTION OF DRAWINGS

To describe technical solutions of the embodiments of the present disclosure more clearly, the accompanying drawings of the embodiments will be briefly introduced in the following. It should be known that the accompanying drawings in the following description merely involve with some embodiments of the present disclosure, but not limit the present disclosure, in which.

DETAILED DESCRIPTION

To make objectives, technical solutions, and advantages of the embodiments of the present disclosure clearer, the technical solutions according to the embodiments of the present disclosure will be described clearly and completely below, in conjunction with the accompanying drawings. Apparently, the described embodiments are some but not all of the embodiments of the present disclosure. All other embodiments obtained by those skilled in the art based on the described embodiments of the present disclosure without creative efforts shall fall within the protection scope of the present disclosure.

Figure 1:
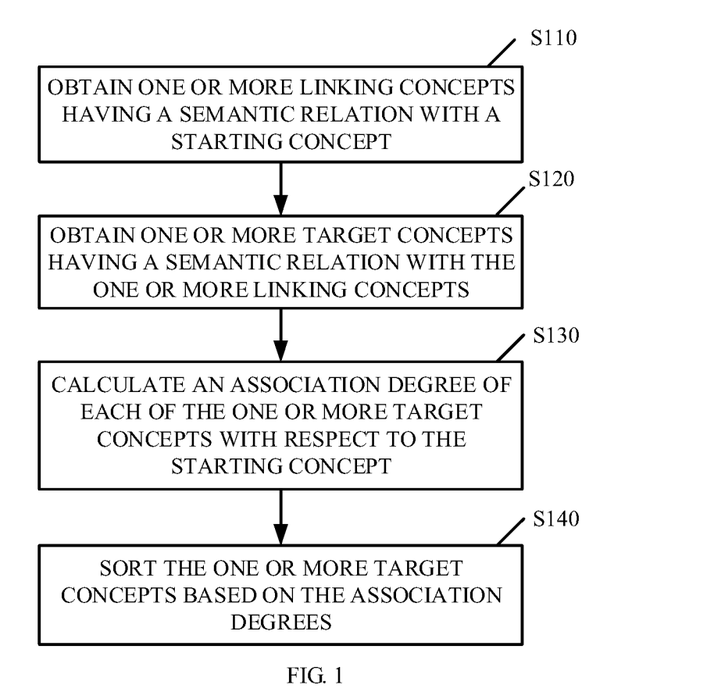
FIG. 1 is a flowchart of a method for automatically discovering medical knowledge according to an embodiment of the present disclosure.

FIG. 1 illustrates a flowchart of a method for automatically discovering medical knowledge according to an embodiment of the present disclosure. In the embodiments of the present disclosure, automatic discovery of medical knowledge is based on the aforementioned ABC model.

As shown in FIG. 1, first of all, one or more linking concepts having a semantic relation with a starting concept are obtained from a medical literature library, in step S110. In embodiments of the present disclosure, the starting concept represents a disease. Next, one or more target concepts having a semantic relation with the one or more linking concepts obtained in step S110 are obtained from the medical literature library, in step S120. Next, an association degree of each of the one or more target concepts with respect to the starting concept is calculated in step S130. The association degree indicates a probability that the target concept can cope with the starting concept. Finally, in step S140, the one or more target concepts are sorted based on the association degrees calculated in step S130.

The method for automatically discovering medical knowledge according to the embodiment as shown in FIG. 1 is described in detail below with reference to FIG. 2, FIG. 3, and FIG. 4.

In step S110 as shown in FIG. 1, the one or more linking concepts having the semantic relation with the starting concept are obtained from the medical literature library based on the inputted starting concept. In embodiments of the present disclosure, the medical literature library is a database for storing medical literatures. The starting concept may be a term representing a disease such as Raynaud's disease, hemicrania, osteoporosis, and so on. FIG. 2 illustrates an exemplary flowchart of a process (step S110) of obtaining the linking concept according to the embodiment as shown in FIG. 1. As shown in FIG. 2, in step S210, a sentence containing the starting concept is retrieved from the medical literature library in response to the input of the starting concept. In embodiments of the present disclosure, an inverted index may be established for the medical literature library, and then the sentence containing the starting concept is retrieved from the medical literatures in the medical literature library using the established inverted index. Next, the semantic relation contained in the retrieved sentence is extracted in step S220. This step may be implemented by performing a semantic analysis on the sentence by using a natural language processing technology. Next, the one or more linking concepts are determined based on the extracted semantic relation in step S230.

For example, when the inputted starting concept is "Raynaud's disease", a sentence such as "some scholars believe that increased blood viscosity is an inducing factor of the Raynaud's disease" may be retrieved from the medical literature library. Next, a semantic analysis is performed on the sentence to extract a semantic relation "inducing (increased blood viscosity, the Raynaud's disease)", which indicates that an inducing relation exists between "increased blood viscosity" and "the Raynaud's disease". Next, "increased blood viscosity" may be determined as the linking concept based on the semantic relation.

It is to be noted that although the semantic relation is described above in the form of "relationship name (concept, concept)", those skilled in the art should understand that other forms (for example, charts, tables, and so on) that can describe the semantic relation between phrases are also applicable herein.

Nevertheless, the linking concept having the semantic relation with the starting concept obtained from the medical literature library in the above process may contain useless information. For example, in the above example "the Raynaud's disease", the linking concept "acral artery spasm" also may be obtained from the retrieved sentence "the Raynaud's disease is also referred to as acral artery spasm". Apparently, this linking concept is useless to discovery of medical knowledge. Therefore, in other embodiments of the present disclosure, after step S230 is performed, the one or more linking concepts determined in step S230 are further filtered in step S240 to obtain the linking concepts having a predetermined semantic relation.

Since the starting concept represents a disease and the target concept is a substance that can cope with (including curing, preventing and so on) the disease, the linking concept generally is a physiological phenomenon caused by the disease according to the ABC model. Therefore, in the embodiments of the present disclosure, the predetermined semantic relation may be as below:

a) an inducing relation, for example, inducing (increased blood viscosity, the Raynaud's disease);

b) an influence relation, for example, influencing (fever, activities of digestive enzymes);

c) an accompanying relation, for example, accompanying (viral influenza, aching all over and fatigued and weak);

d) a causing relation, for example, causing (shock, acid-base disturbance due to reduced pH value); or e) an impairing relation, for example, impairing (ethylism, exchange of substances between nerve cells and ambient environment).

Those skilled in the art should understand that the semantic relation enumerated herein is merely exemplary, and the linking concepts may be filtered using other semantic relations. For example, the predetermined semantic relation may be set by reference to a semantic relation provided by Unified Medical Language System (UMLS) developed by National Library Of Medicine (NLM).

Figure 2:
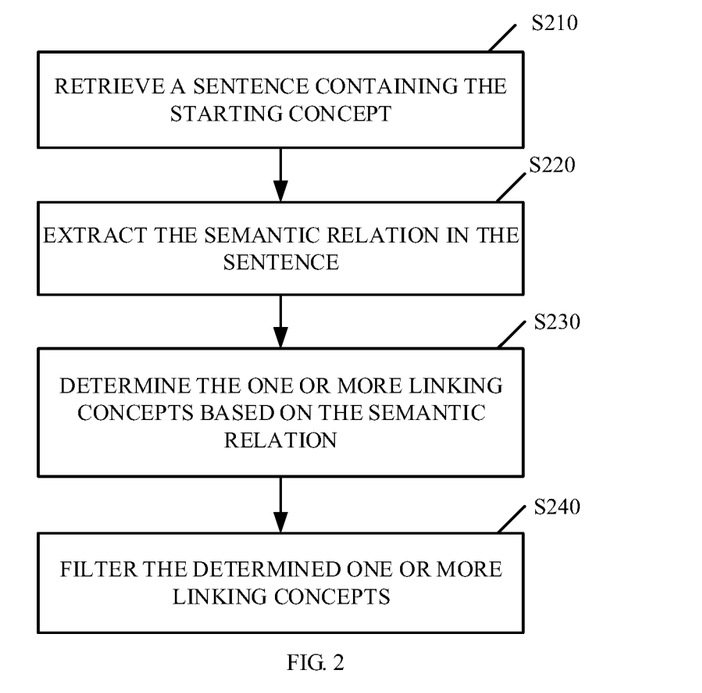
FIG. 2 is an exemplary flowchart of a process of obtaining a linking concept according to the embodiment as shown in FIG. 1.

The one or more linking concepts having the semantic relation with the starting concept may be obtained by way of the process as shown in FIG. 2.

Referring to FIG. 1 again, in step S120, one or more target concepts having a semantic relation with the one or more linking concepts obtained in step S110 are obtained from the medical literature library. FIG. 3 illustrates an exemplary flowchart of a process (step S120) of obtaining a target concept according to the embodiment as shown in FIG. 1. As shown in FIG. 3, for each of the obtained linking concepts, a sentence comprising the linking concept is retrieved from the medical literature library in step S310. Next, in step S320, a semantic analysis is performed on the retrieved sentence to extract the semantic relation contained in the sentence. Next, in step S330, the target concept is determined based on the semantic relation.

In the above example, the linking concept is determined as "increased blood viscosity". Therefore, a sentence "deep sea fish oil is conducive to suppressing the increased blood viscosity" may be retrieved from the medical literature library. The semantic relation "suppressing (deep sea fish oil, increased blood viscosity)" may be extracted from this sentence by semantic analysis. Hence, the determined target concept is "deep sea fish oil".

Figure 3:
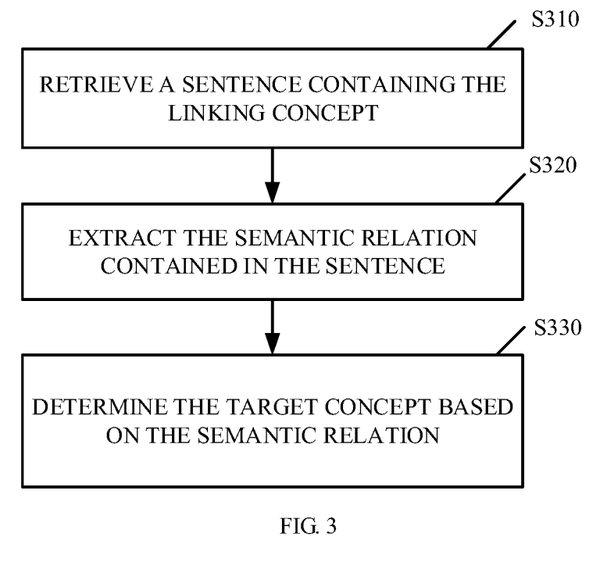
FIG. 3 is an exemplary flowchart of a process of obtaining a target concept according to the embodiment as shown in FIG. 1.

The one or more target concepts having the semantic relation with the obtained linking concepts may be obtained by way of the process as shown in FIG. 3.

After the linking concepts and the target concepts are obtained, an association degree of each of the one or more target concepts with respect to the starting concept is calculated in step S130. In embodiments of the present disclosure, the association degree indicates a probability that the target concept can cope with (including curing, preventing and so on) the starting concept. The probability that the target concept can cope with the starting concept can be determined based on the association degree, such that the importance of the target concept is determined.

In embodiments of the present disclosure, a Markov logic network may be used to compute the association degree. The Markov logic network is probabilistic extension of first-order logic and can depict complex dependency relations among things. Specifically, the Markov logic network is a set of a series of first-order logic clauses having weights. The Markov logic network may define a Markov random field. In the Markov logic network, a vertex represents a ground predicate or ground atom, and a feature represents a ground formula. If the ground predicate (or ground atom) is true, its value may be set to 1, otherwise its value may be set to 0. If the ground formula is true, its value may be set to 1, otherwise its value may be set to 0. Each feature may have a weight to reflect the importance of the feature. Therefore, the probability of the possible world X contained in a closed Markov logic network may be expressed as below:

$$P(X) = \frac{1}{Z}\exp(\Sigma_i\ w_i f_i(X)) \quad (1)$$

wherein, X represents the possible world contained in the ground Markov logic network, Z represents a normalization factor, $f_i$ represents the $i^{th}$ feature, corresponding to first-order logic formulas, and $w_i$ represents a weight for the $i^{th}$ feature $f_i$.

The suitable Markov logic network needs to be pre-established and trained to calculate the association degree of the target concept with respect to the starting concept by using the Markov logic network.

First, predicates serving as the vertexes of the Markov logic network and the first-order logic formulas serving as the features are set. In the following description, the symbol dis (disease) represents a disease, the symbol phy (physiological function) represents a physiological function, and the symbol sub (substance) represents a substance.

Some examples of the predicates and the first-order logic formulas are given below.

The predicates may be, for example, as below:

Prevent (i, j), used for determining whether i can prevent j. If i can prevent j, its value is set to true, otherwise its value is set to false.

Type (i, c), used for determining whether the semantic type of i is c. If the semantic type of i is c, its value is set to true, otherwise its value is set to false.

Contain (m1, i), used for determining whether m1 contains i. If m1 contains i, its value is set to true, otherwise its value is set to false.

hasRelation (i, j, r), used for determining whether a relation r exists between i and j. If the relation r exists between i and j, its value is set to true, otherwise its value is set to false.

hasPhy(k), used for determining whether a certain physiological function k is selected. If the physiological function k is selected, its value is set to true, otherwise its value is set to false.

hasSub(i), used for determining whether a certain substance i is selected. If the substance i is selected, its value is set to true, otherwise its value is set to false.

The first-order logic formulas may be, for example, as below:

hasPhy(k)=>Type(k, *), which indicates that if the physiological function k is selected, the k necessarily has a certain semantic type, wherein * represents an arbitrary semantic type, and => represents an containing relation.

hasSub(i)=>Type(i, *), which indicates that if the substance i is selected, the i necessarily has a certain semantic type.

|Type(k, *)|≤1, which indicates that the physiological function k at most has one semantic type.

|Type(i, *)|≤1, which indicates that the substance i at most has one semantic type.

hasPhy(k)∧Type(k, phy)∧hasRelation(k, d,"inducing")∧hasSub(i)∧Type(i, sub)∧hasRelation(i, k,"suppressing")=>Prevent(i, d), which indicates that if the physiological function k can induce a disease d, the substance i can suppress the physiological function k, the substance i may prevent certain disease d.

hasPhy(k)∧Type(k, phy)∧hasRelation(k, d,"inducing")∧hasSub(i)∧Type(i, sub)∧hasRelation(i, k,"suppressing")∧Countain(m, i)∧Type(m, sub)=>Prevent(m, d), which indicates that if the physiological function k can induce a disease d, the substance i can suppress the physiological function k, and a substance m contains the substance i, the substance m may prevent the disease d.

hasPhy(k)∧Type(k, phy)∧hasRelation(d, k,"accompanying")∧hasSub(i)∧Type(i, sub)∧hasRelation(i, k,"alleviating")=>Prevent(i, d), which indicates that if the disease d is accompanied by the physiological function k and the substance i can alleviate the physiological function k, the substance i may prevent the disease d.

hasPhy(k)∧Type(k, phy)∧hasRelation(d, k,"accompanying")∧hasSub(i)∧Type(i, sub)∧hasRelation(i, k,"alleviating")∧Countain(m, i)∧Type(m, sub)=>Prevent(m, d), which indicates that if the disease d is accompanied by the physiological function k, the substance i can alleviate the physiological function k, and the substance m contains the substance i, the substance m may prevent the disease d.

hasPhy(k)∧Type(k, phy)∧hasRelation(d, k,"influence")∧hasSub(i)∧Type(i, sub)∧hasRelation(i, k,"stimulating")=>Prevent(i, d), which indicates that if the disease d has an influence on the physiological function k and the substance i can stimulate the physiological function k, the substance i may prevent the disease d.

hasPhy(k)∧Type(k, phy)∧hasRelation(d, k,"influence")∧hasSub(i)∧Type(i, sub)∧hasRelation(i, k,"stimulating")∧Contain(m, i)∧Type(m, sub)=>Prevent(m, d), which indicates that if the disease d has an influence on the physiological function k, the substance i can stimulate the physiological function k, and the substance m contains the substance i, the substance m may prevent the disease d.

Contain(m, i)∧Prevent(i, j)=>Prevent(m, j), which indicates that if the substance m contains the substance i and the substance i can prevent j, the substance m can prevent the j.

It is to be noticed that the predicates and the first-order logic formulas listed above are merely exemplary, and those skilled in the art knows that other predicates and first-order logic formulas may be set as required.

After the Markov logic network is established based on the predicates and the first-order logic formulas, the Markov logic network may be trained by using existing medical knowledge to determine the weight for each of the first-order logic formulas. The Markov logic network may be trained using an existing training method, which is well known to those skilled in the art.

Figure 4:
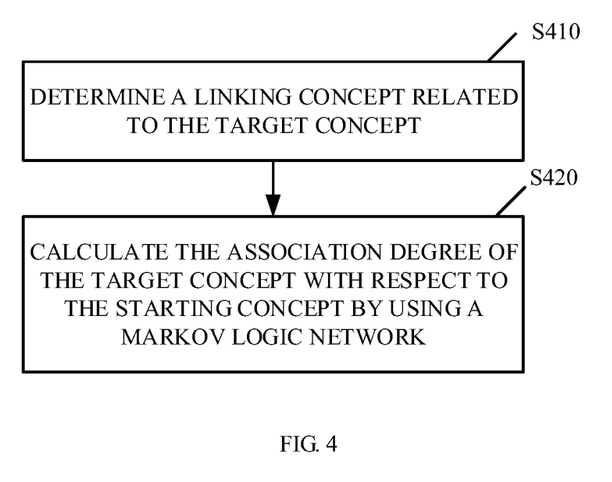
FIG. 4 is an exemplary flowchart of a process of calculating an association degree of a target concept with respect to a starting concept according to the embodiment as shown in FIG. 1.

FIG. 4 illustrates an exemplary flowchart of a process of calculating an association degree of a target concept with respect to a starting concept according to the embodiment as shown in FIG. 1. As shown in FIG. 4, for each of the obtained target concept, in step S410, a linking concept related to the target concept in the obtained linking concepts is determined as a related linking concept for the target concept. In embodiments of the present disclosure, for one starting concept, one or more linking concepts may be obtained, whereas for each of the one or more linking concepts, one or more target concepts may be obtained. Therefore, one target concept may correspond to one or more linking concepts (namely, the related linking concepts). With this step, the related linking concepts used for specific target concepts may be determined. Next, in step S420, the association degree of the target concept with respect to the starting concept may be calculated based on a first semantic relation between the determined related linking concept and the starting concept and a second semantic relation between the related linking concept and the target concept, by using a pretrained Markov logic network. As previously described, the Markov logic network is composed of predicates and first-order logic formulas. In the well-trained Markov logic network, the weight for each of the first-order logic formulas has been determined. In this way, the related predicates and the first-order logic formulas may be determined in the Markov logic network based on the starting concept, the target concept, the first semantic relation and the second semantic relation, and then the association degree of the target concept with respect to the starting concept may be calculated based on the Formula (2).

$$P = \frac{1}{Z}\exp(\Sigma_i \, w_i f_i) \quad (2)$$

wherein P represents the association degree, Z represents a normalization factor, $f_i$ represents the $i^{th}$ logic formula, and $w_i$ represents a weight for the $i^{th}$ logic formula.

For each of the target concepts, steps S410 and S420 are executed to calculate the association degree of each of the target concepts with respect to the starting concept.

Returning to FIG. 1, in step S140, the target concepts are sorted based on the association degree, calculated in step S130, of each of the target concepts with respect to the starting concept. In embodiments of the present disclosure, the target concepts are sorted according to a descending order of the corresponding association degrees. In this way, those target concepts having higher association degrees are ranked ahead, and thus the probability of discovering useful medical knowledge is increased.

As can be seen from the above description, by using the method for automatically discovering medical knowledge in this embodiment, potential medical knowledge may be discovered from the medical literature library by using natural language processing technologies and the Markov logic network, and the importance of the medical knowledge is determined. In this way, the probability of discovering useful medical knowledge is increased.

Figure 5:
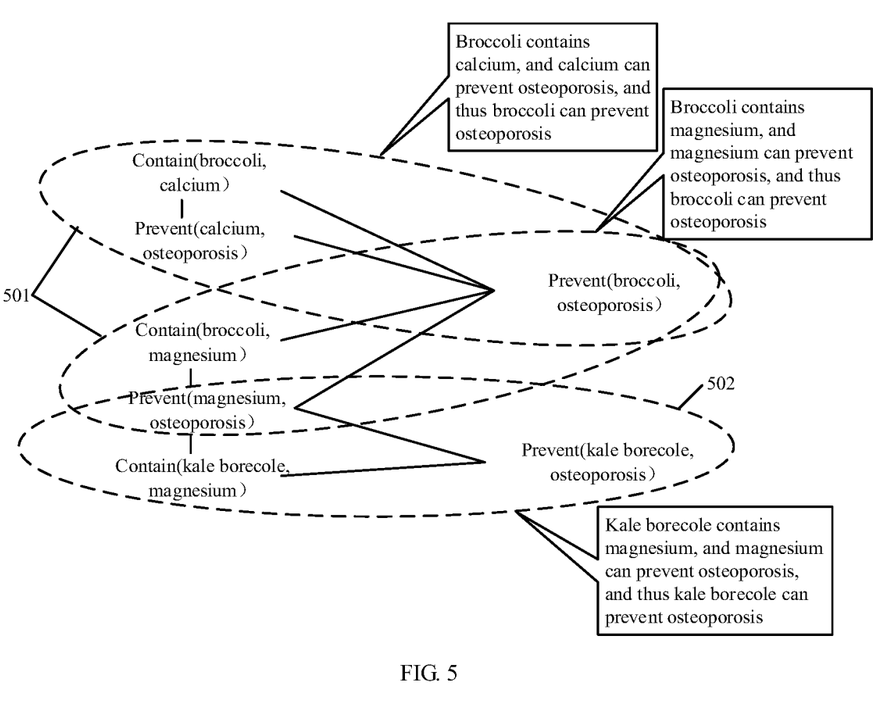
FIG. 5 is a schematic diagram illustrating an example where an association degree of a target concept with respect to a starting concept is calculated by using a Markov logic network.

FIG. 5 is a schematic diagram illustrating an example where an association degree of a target concept with respect to a starting concept is calculated by using the Markov logic network. In this example, the starting concept is "osteoporosis", the linking concepts are "calcium" and "magnesium", and the target concepts are "broccoli" and "kale borecole". For the target concept "broccoli", the related linking concepts are "calcium" and "magnesium". Therefore, the corresponding first semantic relation is "calcium can prevent osteoporosis" and "magnesium can prevent osteoporosis", and the second semantic relation is "broccoli contains calcium" and "broccoli contains magnesium". For the target concept "kale borecole", the related linking concept is "magnesium". Therefore, the corresponding first semantic relation is "magnesium can prevent osteoporosis", and the second semantic relation is "kale borecole contains magnesium". Furthermore, the weight for the first-order logic formula Contain(m, i) ∧ Prevent(i, j)=>Prevent(m, j) in the Markov logic network is determined as 1.5.

Therefore, in the Markov logic network, portions determined based on the starting concept "osteoporosis", the target concept "broccoli" as well as the first semantic relation and the second semantic relation are as shown in the ellipses 501 in FIG. 5; and portions determined based on the starting concept "osteoporosis", the target concept "kale borecole" as well as the first semantic relation and the second semantic relation are as shown in the ellipse 502 in FIG. 5.

Therefore, based on the above Formula (2), the association degree P (broccoli can prevent osteoporosis) of broccoli with respect to osteoporosis i.e., the probability that broccoli can prevent osteoporosis may be calculated, as below:

$$P(\text{broccoli can prevent osteoporosis}) = \frac{1}{Z}\exp(1.5 + 1.5).$$

The association degree P (kale borecole can prevent osteoporosis) of kale borecole with respect to osteoporosis may be calculated as below:

$$P(\text{broccoli can prevent osteoporosis}) = \frac{1}{Z}\exp(1.5).$$

Therefore, based on the calculated association degree, the target concept "broccoli" is ranked ahead of the target concept "kale borecole".

Figure 6:
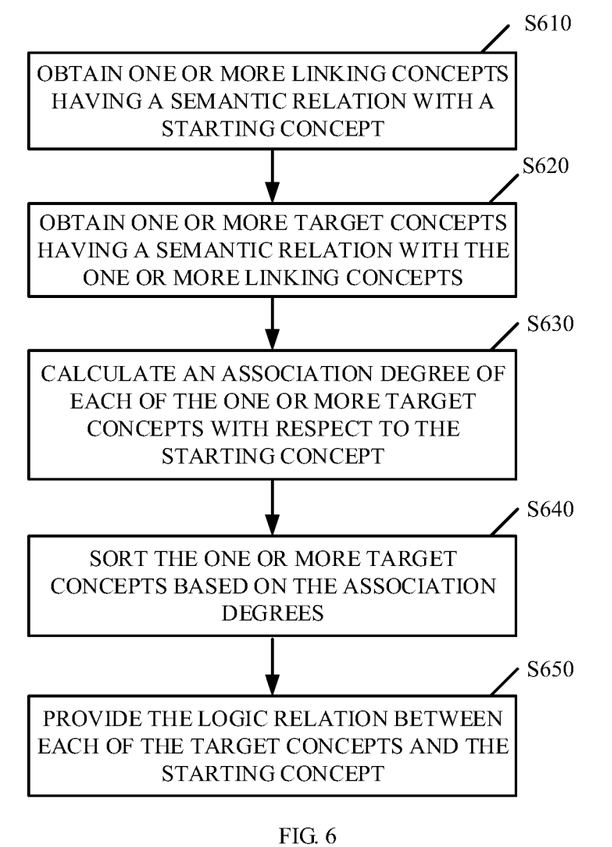
FIG. 6 is a flowchart of a method for automatically discovering medical knowledge according to another embodiment of the present disclosure.

FIG. 6 is a flowchart of a method for automatically discovering medical knowledge according to another embodiment of the present disclosure. Compared with the embodiment as shown in FIG. 1, in the embodiment as shown in FIG. 6, after the target concepts are sorted, a logic relation between each of the target concepts and the starting concept may be provided.

As shown in FIG. 6, steps S610-S640 are the same as steps S110-S140 as shown in FIG. 1, and thus the description thereof is omitted herein.

After the target concepts are sorted, the logic relation between each of the target concepts and the starting concept is provided in step S650. In some embodiments of the present disclosure, for each of the target concepts, the first-order logic formulas involved from the starting concept to the target concept may be determined as the logic relation. The first-order logic formula may be determined based on the second semantic relation between the target concept and the related linking concept as well as the first semantic relation between the starting concept and the related linking concept. For example, in the above example, for the starting concept "osteoporosis" and the target concept "broccoli", the first semantic relation is "calcium can prevent osteoporosis" and "magnesium can prevent osteoporosis", and the second semantic relation is "broccoli contains calcium" and "broccoli contains magnesium". Therefore, the corresponding first-order logic formula is as below: Contain(broccoli, calcium)∧Prevent(calcium, osteoporosis)=>Prevent(broccoli, osteoporosis) and Contain(broccoli, magnesium)∧Prevent(magnesium, osteoporosis)=>Prevent(broccoli, osteoporosis). Next, the determined logic relation may be recorded in association with the target concept.

In the above example, the sorting of the target concepts and the logic relation between the each of the target concepts and the starting concept may be illustrated as shown in Table 1.

TABLE 1

| Target concepts | Association degree | Logic relation |
| --- | --- | --- |
| Broccoli | $P = \frac{1}{Z}\exp(1.5 + 1.5)$ | 1. Broccoli contains calcium, and calcium can prevent osteoporosis, and thus broccoli can prevent osteoporosis; and<br>2. Broccoli contains magnesium, and magnesium can prevent osteoporosis, and thus broccoli can prevent osteoporosis. |
| Kale borecole | $P = \frac{1}{Z}\exp(1.5)$ | 1. Kale borecole contains magnesium, and magnesium can prevent osteoporosis, and thus kale borecole can prevent osteoporosis. |

As can be seen from the above description, the method for automatically discovering medical knowledge according to this embodiment can further provide the logic relation between the target concept and the starting concept, such that the explainability of the medical knowledge is improved.

Figure 7:
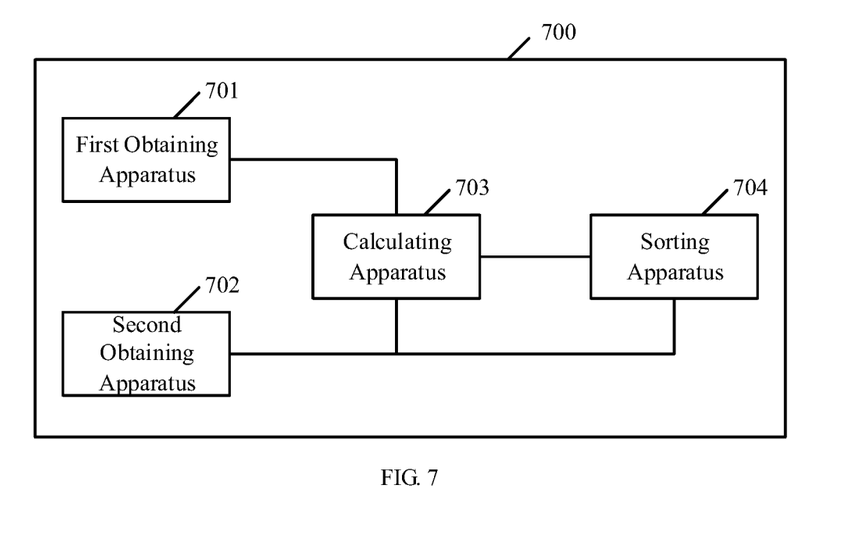
FIG. 7 is a schematic block diagram of a system for automatically discovering medical knowledge according to an embodiment of the present disclosure.
Figure 8:
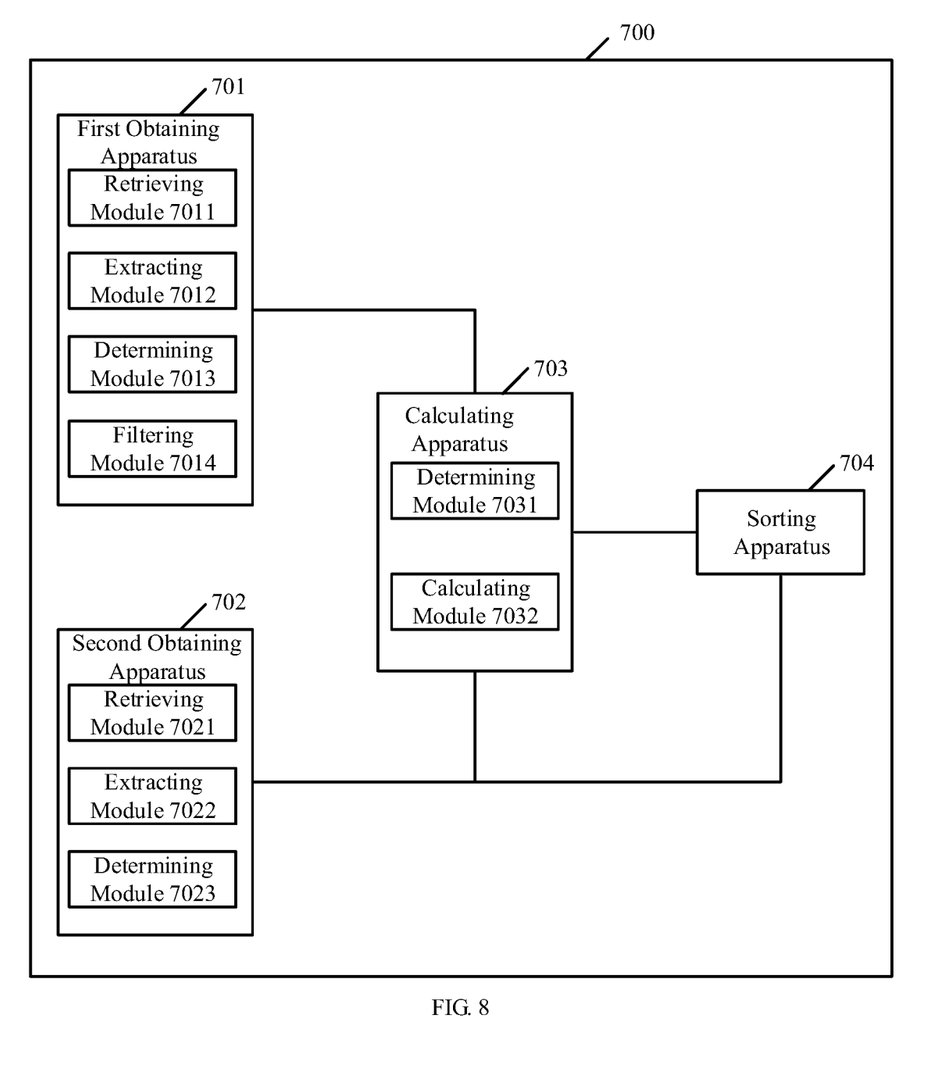
FIG. 8 is an exemplary embodiment of a schematic block diagram of the system for automatically discovering medical knowledge as shown in FIG. 7.

FIG. 7 illustrates a schematic structure of a system 700 for automatically discovering medical knowledge according to an embodiment of the present disclosure, and FIG. 8 illustrates an example of specific implementation of the system 700. The system 700 for automatically discovering medical knowledge is described below in detail with reference to FIG. 7 and FIG. 8, and description of portions the same as those in the preceding embodiments is properly omitted.

As shown in FIG. 7, the system 700 may include a first obtaining apparatus 701, a second obtaining apparatus 702, a calculating apparatus 703, and a sorting apparatus 704.

The first obtaining apparatus 701 may obtain one or more linking concepts having a semantic relation with a starting concept from a medical literature library. As previously mentioned, the starting concept may represent a disease. Referring to FIG. 8, in the first obtaining apparatus 701, a retrieving module 7011 may retrieve a sentence containing the inputted starting concept from the medical literature library. Next, an extracting module 7012 may extract the semantic relation contained in the retrieved sentence, and a determining module 7013 determines the one or more linking concepts based on the semantic relation.

Moreover, the first obtaining apparatus 701 may further include a filtering module 7014. The filtering module 7014 may filter the obtained linking concepts to obtain the linking concepts having a predetermined semantic relation.

The second obtaining apparatus 702 may obtain, from the medical literature library, one or more target concepts having a semantic relation with the one or more linking concepts obtained by the first obtaining apparatus 701. Referring to FIG. 8, in the second obtaining apparatus 702, a retrieving module 7021 may retrieve, for each of the obtained one or more linking concepts, a sentence containing the starting concept from the medical literature library. Next, for each sentence retrieved, an extracting module 7022 may extract the semantic relation contained in the sentence, and a determining module 7023 determines the one or more target concepts based on the extracted semantic relation.

The calculating apparatus 703 may calculate an association degree of each of the one or more target concepts, obtained by the second obtaining apparatus 702, with respect to the starting concept. As previously mentioned, the association degree indicates a probability that the target concept can cope with the starting concept. As shown in FIG. 8, in the calculating apparatus 703, a determining module 7031 may determine, for each of the determined one or more target concepts, a linking concept related to the target concept in the one or more linking concepts as a related linking concept. Next, a calculating module 7032 may calculate the association degree of the target concept with respect to the starting concept based on a first semantic relation between the related linking concept and the starting concept and a second semantic relation between the related linking concept and the target concept by using a pretrained Markov logic network. As previously described, the Markov logic network may be composed of predefined predicates and logic formulas describing a logic relation among the predicates. In embodiments of the present disclosure, the association degree may be calculated based on Formula (2).

The sorting apparatus 704 may sort the one or more target concepts based on the calculated association degrees. In embodiments of the present disclosure, the sorting apparatus 704 may sort the one or more target concepts according to a descending order of the corresponding association degrees.

Moreover, in other embodiments of the present disclosure, the system 700 may further include a providing apparatus, which may provide a logic relation between each of the one or more target concepts and the starting concept. In one embodiment, the providing apparatus may include a logic relation determining module and a recording module. The logic relation determining module may determine, for each of the determined one or more target concepts, a logic formula including the first semantic relation and the second semantic relation as the logic relation between the target concept and the starting concept. Next, the recording module may record the determined logic relation in association with the target concept.

It should be noted that the system 700 as shown in FIG. 7 and FIG. 8 can be operable to implement the method for automatically discovering medical knowledge as shown in FIGS. 1-4 and FIG. 6.

Figure 9:
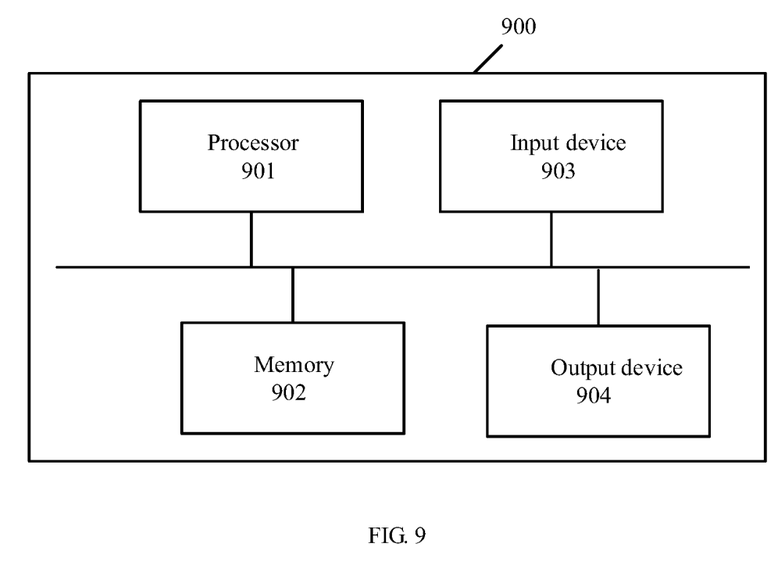
FIG. 9 is a schematic block diagram of an apparatus for automatically discovering medical knowledge according to another embodiment of the present disclosure.

FIG. 9 illustrates an apparatus 900 for automatically discovering medical knowledge according to another embodiment of the present disclosure. As shown in FIG. 9, the apparatus 900 may include a processor 901 and a memory 902 storing a computer program. When the computer program is executed by the processor 901, the apparatus 900 is caused to perform the steps of the method for automatically discovering medical knowledge as shown in FIG. 1. That is, the apparatus 900 may obtain one or more linking concepts having a semantic relation with a starting concept from a medical literature library, and obtain one or more target concepts having a semantic relation with the one or more obtained linking concepts from the medical literature library. Next, the apparatus 900 may calculate an association degree of each of the one or more target concepts with respect to the starting concept, and sort the one or more target concepts based on the calculated association degrees.

The association degree indicates a probability that the target concept can cope with the starting concept.

In embodiments of the present disclosure, the apparatus 900 may determine, for each of the one or more target concepts, a linking concept related to the target concept in the one or more linking concepts as a related linking concept. Next, the apparatus 900 may calculate the association degree of the target concept with respect to the starting concept based on a first semantic relation between the related linking concept and the starting concept and a second semantic relation between the related linking concept and the target concept by using a pretrained Markov logic network. The Markov logic network is composed of predefined predicates and logic formulas describing a logic relation among the predicates.

In embodiments of the present disclosure, the apparatus 900 may calculate the association degree of the target concept with respect to the starting concept based on the formula as below:

$$P = \frac{1}{Z}\exp(\Sigma_i\ w_i f_i)$$

wherein P represents the association degree, Z represents a normalization factor, $f_i$ represents the $i^{th}$ logic formula, and $w_i$ represents a weight for the $i^{th}$ logic formula.

In embodiments of the present disclosure, the apparatus 900 may also provide a logic relation between each of the one or more target concepts and the starting concept.

In embodiments of the present disclosure, the apparatus 900 may determine, for each of the one or more target concepts, a logic formula including the first semantic relation and the second semantic relation as the logic relation. Next, the apparatus 900 may record the logic relation in association with the target concept.

In embodiments of the present disclosure, the apparatus 900 may retrieve a sentence containing the starting concept from the medical literature library. Next, the apparatus 900 may extract a semantic relation contained in the sentence, and determine the one or more linking concepts based on the extracted semantic relation.

In embodiments of the present disclosure, the apparatus 900 may also filter the obtained linking concepts to obtain the linking concepts having a predetermined semantic relation.

In embodiments of the present disclosure, the apparatus 900 may retrieve, for each of the one or more linking concepts, a sentence containing the linking concept from the medical literature library. Next, the apparatus 900 may extract the semantic relation contained in the sentence, and determine the one or more target concepts based on the extracted semantic relation.

In embodiments of the present disclosure, the apparatus 900 may sort the one or more target concepts according to a descending order of the corresponding association degrees.

In embodiments of the present disclosure, the processor 901 may be, for example, a central processing unit (CPU), a microprocessor, a digital signal processor (DSP), a processor based on a multi-core processor architecture, and so on. The memory 902 may be a memory of any type that is implemented by using a data storage technology, including but not limited to a random access memory, a read-only memory, a semiconductor-based memory, a flash memory, a magnetic disk memory, and so on.

Furthermore, in the embodiments of the present disclosure, the apparatus 900 may also include an input device 903 such as a keyboard or a mouse to input the starting concept. Moreover, the apparatus 900 may also include an output device 904 such as a display to output the sorting of the target concepts and the logic relation thereof.

In embodiments of the present disclosure, there is also provided a computer readable storage medium storing a computer program. When the computer program is executed by the processor, the steps of the method for automatically discovering medical knowledge as shown in FIGS. 1-4 and FIG. 6 are carried out.

Although a plurality of embodiments of the present disclosure have been illustrated in the accompanying drawings and set forth in the above detailed description, it is to be understood that the present disclosure is not limited to the disclosed embodiments, instead the present disclosure may be redeployed, modified and substituted without departing from the scope of the present disclosure limited by the claims.

What is claimed is:

1. A computer-implemented method for automatically discovering medical knowledge comprising: obtaining, by at least one processor, one or more linking concepts having a semantic relation with a starting concept from a medical literature library, wherein the starting concept represents a disease; obtaining, by at the least one processor, one or more target concepts having a semantic relation with the one or more linking concepts from the medical literature library; calculating, by at the least one processor, an association degree of each of the one or more target concepts with respect to the starting concept, wherein the association degree indicates a probability that the target concept is able to cope with the starting concept; and sorting, by at the least one processor, the one or more target concepts according to the calculated association degrees; and displaying the sorting of the target concepts, wherein calculating the association degree of each of the one or more target concepts with respect to the starting concept comprises: for each of the one or more target concepts, determining, by the at least one processor, a linking concept related to the target concept in the one or more linking concepts as a related linking concept and calculating, by the at least one processor, the association degree of the target concept with respect to the starting concept based on a first semantic relation between the related linking concept and the starting concept and a second semantic relation between the related linking concept and the target concept by using a pretrained Markov logic network, wherein the Markov logic network is composed of predefined predicates and logic formulas describing a logic relation among the predicates.

2. The method according to claim 1, wherein the association degree of the target concept with respect to the starting concept is calculated as below:

$$P = \frac{1}{Z}\exp(\Sigma_i\ w_i f_i)$$

wherein P represents the association degree, Z represents a normalization factor, $f_i$ represents the $i^{th}$ logic formula, and $w_i$ represents a weight for the $i^{th}$ logic formula.

3. The method according to claim 1, further comprising: providing a logic relation between each of the one or more target concepts and the starting concept.

4. The method according to claim 3, wherein providing a logic relation between each of the one or more target concepts and the starting concept comprises: for each of the one or more target concepts, determining a logic formula including the first semantic relation and the second semantic relation as the logic relation; and recording the logic relation in association with the target concept.

5. The method according to claim 1, wherein obtaining one or more linking concepts having the semantic relation with the starting concept from the medical literature library comprises: retrieving a sentence containing the starting concept from the medical literature library; extracting the semantic relation contained in the sentence; and determining the one or more linking concepts based on the semantic relation.

6. The method according to claim 5, wherein obtaining one or more linking concepts having the semantic relation with the starting concept from the medical literature library further comprises: filtering the obtained linking concepts to obtain the linking concepts having a predetermined semantic relation.

7. The method according to claim 1, wherein obtaining one or more target concepts having the semantic relation with the one or more linking concepts from the medical literature library comprises: for each of the one or more linking concepts, retrieving a sentence containing the linking concept from the medical literature library; extracting the semantic relation contained in the sentence; and determining the target concept based on the semantic relation.

8. The method according to claim 1, wherein the one or more target concepts are sorted according to a descending order of the corresponding association degrees.

9. An apparatus for automatically discovering medical knowledge comprising: at least one processor; and at least one memory storing a computer program; wherein when the computer program is executed by the at least one processor, the apparatus is caused to:
obtain one or more linking concepts having a semantic relation with a starting concept from a medical literature library, wherein the starting concept represents a disease; obtain one or more target concepts having a semantic relation with the one or more linking concepts from the medical literature library; calculate an association degree of each of the one or more target concepts with respect to the starting concept, wherein the association degree indicates a probability that the target concept is able to cope with the starting concept; and sort the one or more target concepts according to the calculated association degrees,
wherein the apparatus further comprise a display device configured to display the sorting of the target concepts, and
wherein when the computer program is executed by the at least one processor, the apparatus is caused to calculate the association degree of each of the one or more target concepts with respect to the starting concept by the following operations: for each of the one or more target concepts,
determining a linking concept related to the target concept in the one or more linking concepts as a related linking concept; and
calculating the association degree of the target concept with respect to the starting concept based on a first semantic relation between the related linking concept and the starting concept and a second semantic relation between the related linking concept and the target concept by using a pretrained Markov logic network, wherein the Markov logic network is composed of predefined predicates and logic formulas describing a logic relation among the predicates.

10. The apparatus according to claim 9, wherein the association degree of the target concept with respect to the starting concept is calculated as below:

$$P = \frac{1}{Z}\exp(\Sigma_i \ w_i f_i)$$

wherein P represents the association degree, Z represents a normalization factor, $f_i$ represents the $i^{th}$ logic formula, and $w_i$ represents a weight for the $i^{th}$ logic formula.

11. The apparatus according to claim 9, wherein when the computer program is executed by the at least one processor, the apparatus is further caused to provide a logic relation between each of the one or more target concepts and the starting concept.

12. The apparatus according to claim 11, wherein when the computer program is executed by the at least one processor, the apparatus is caused to provide a logic relation between each of the one or more target concepts and the starting concept by the following operations: for each of the one or more target concepts, determining a logic formula including the first semantic relation and the second semantic relation as the logic relation; and recording the logic relation in association with the target concept.

13. The apparatus according to claim 9, wherein when the computer program is executed by the at least one processor, the apparatus is caused to obtain one or more linking concepts having the semantic relation with the starting concept from the medical literature library by the following operations: retrieving a sentence containing the starting concept from the medical literature library; extracting the semantic relation contained in the sentence; and determining the one or more linking concepts based on the semantic relation.

14. The apparatus according to claim 13, wherein when the computer program is executed by the at least one processor, the apparatus is further caused to obtain one or more linking concepts having the semantic relation with the starting concept from the medical literature library by the following operation: filtering the obtained linking concepts to obtain the linking concepts having a predetermined semantic relation.

15. The apparatus according to claim 9, wherein when the computer program is executed by the at least one processor, the apparatus is caused to obtain one or more target concepts having the semantic relation with the one or more linking concepts from the medical literature library by the following operations: for each of the one or more linking concepts, retrieving a sentence containing the linking concept from the medical literature library; extracting the semantic relation contained in the sentence; and determining the target concept based on the semantic relation.

16. The apparatus according to claim 9, wherein when the computer program is executed by the at least one processor, the apparatus is caused to sort the one or more target concepts according to a descending order of the corresponding association degrees.

17. A computer readable non-transitory storage medium storing a computer program, wherein when the computer program is executed by a processor, the steps of the method for automatically discovering medical knowledge according to claim 1 are carried out.

18. The method according to claim 2, further comprising: providing a logic relation between each of the one or more target concepts and the starting concept.

\* \* \* \* \*